US00PP08323P

United States Patent [19]

Vletter

[11] Patent Number: Plant 8,323

[45] Date of Patent: Jul. 27, 1993

[54] LILY PLANT NAMED NOVE CENTO

[75] Inventor: Floris Vletter, Rijnsburg, Netherlands

[73] Assignee: Gebr. Vletter & J.A., Rijnsburg, Netherlands

[21] Appl. No.: 795,954

[22] Filed: Nov. 21, 1991

[51] Int. Cl.[5] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A new cultivar of lily plant named Nove Cento, characterized by its bright uniform yellow flower color with few markings, vigorous growth habit, numerous medium long and narrow leaves, and medium to tall stems.

1 Drawing Sheet

The present invention comprises a new and distinct cultivar of lily, botanically known as Lilium, commercially known as Lilium asiastic hybrid, and hereinafter referred to by the cultivar name Nove Cento. The parents were asiatic varieties belonging to division I described in "Classification of Lily Cultivars into Divisions" published by Victoria Mathews, The Royal Botanic Gardens, Kew (1989).

The new cultivar is a product of a planned breeding program which had the primary objective of creating new lily cultivars having yellow flower color but otherwise expressing the desirable phenotypic characteristics of the cultivar L'Avingnon.

The new cultivar was originated from a hybridization made by the inventor in a controlled breeding program in Rijnsburg, The Netherlands in 1984. The male parent was an unnamed seedling, and the female parent was Avignon.

The new cultivar was discovered and selected as one flowering plant within the progeny of the stated cross by the inventor in June 1984 in a controlled environment in Rijnsburg, The Netherlands.

The first act of asexual reproduction of the new cultivar was accomplished by the inventor when scales were taken from the initial selection in 1987 in a controlled environment in Rijnsburg, The Netherlands.

Horticultural examination of selected units has demonstrated that the combination of characteristics as herein disclosed for the new cultivar are firmly fixed and are retained through successive generations of asexual reproduction.

The new cultivar has not been observed under all possible environmental conditions. The phenotype may vary significantly with variations in environment such as temperature, light intensity, and day length, without, however, any variation in genotype. The following observations, measurements and comparisons describe plants grown in Wageningen and Rijnsburg, The Netherlands under greenhouse conditions which approximate those generally used in commercial practice.

The following traits have been repeatedly observed and are determined to be basic characteristics of the new cultivar which in combination distinguish this lily as a new and distinct cultivar.

1. Uniform bright yellow flower color.
2. Very little marking or spotting, with a few spots appearing near the base of each tepal.
3. Numerous medium long and narrow leaves.
4. Vigorous growth habit.

5. Medium to tall stems.

Of the many commercial cultivars known to the present inventor, the most similar in comparision to the new cultivar is London. In comparision to London, Nove Cento blooms earlier, is less tall, and has fewer marks or spots on its bright yellow tepals. When flowering is forced under natural light, Nove Cento produces an inflorescence approximately 44 days earlier than Stargazer, under the same growing conditions. Nove Cento is fertile.

The accompanying photographic drawing shows typical flower characteristics of the new cultivar, with colors being as true as possible with illustrations of this type. The photograph comprises a top perspective view showing two open flowers and several buds at various stages.

In the following description, color references are made to The Royal Horticultural Society (R.H.S.) Colour Chart. The color values were determined at Wageningen in 1989–1990 and Rijnsburg in July 1991.

Origin: Seedling from Breeding Program.

Parentage:

*Seed parent.*—Avignon.

*Pollen parent.*—Unnamed seeding.

Classification:

*Botanical.*—Lilium.

*Commercial.*—Asiatic hybrid.

The Plant:

*Form.*—A single stem carrying numerous pedicels alternately arranged.

*Height.*—Medium to tall; 125 cm at time of opening of anthers of first flower.

*Growth habit.*—Vigorous.

*Stem.*—Grooved in transverse section; no anthocyanin pigmentation; internodal length uniform, 2 cm; color 144B.

*Foliage.*—Quantity: 75–95 leaves, depending on growing conditions. Size of leaf: Mature leaves are medium in length (15 cm), and narrow to medium in width (2 cm). Shape of leaves: Elliptical. Texture: Smooth with strong glossiness; no pubescence. Color: Medium green 137B.

*Bulbs.*—Size: Outlet 6–22 cm. Color: White and yellow.

*Roots.*—Both stem and contractible present.

The Bud:

*Form.*—Tapering (like a lancet).

*Size.*—8 cm prior to opening.

*Opening.*—Unfolds normally.
*Color.*—Yellow 1B.
*Tepals.*—Folded, three visible.

The Flower:

*Blooming habit.*—Raceme.
*Size.*—14 cm in total diameter, depending on growing conditions.
*Borne.*—Upright to horizontal.
*Shape.*—Generally in form of hexagonal star; bowl-shaped in cross-section.
*Tepalage.*—Number of tepals: Six. Arrangement: Three inner and three outer. Color: Upper surface: Bright yellow 12A. Lower surface: Yellow 13B with tinge of green-red. Spotting or markings: Very few dark red spots lower half of tepals dispersed near center, each 1-2 mm.
*Nectaries and papillae.*—Present.
*Pedicel.*—Length: 15 cm of first flower. Color: Medium green. Form: Generally straight.
*Texture.*—Ribbed and papillose.

*Disease resistance.*—No disease problems noted to date.
*Fragrance.*—Absent.
*Lasting quality.*—Excellent.

Reproductive Organs:

*Stamens, anthers.*—Arrangement: Anthers form a generally circular pattern. Length: Short, 6 cm. Number: Six. Filaments: Yellow.
*Pollen color.*—Orange.
*Anther color.*—Orange brown.
*Pistils.*—Yellow-green style; total length pistil 7 cm.
*Stigma.*—Yellow.
*Ovaries.*—Triangular in shape, other characteristics typical of asiatic lily varieties.

I claim:

1. A new and distinct cultivar of lily plant named Nove Cento, as illustrated and described.

* * * * *

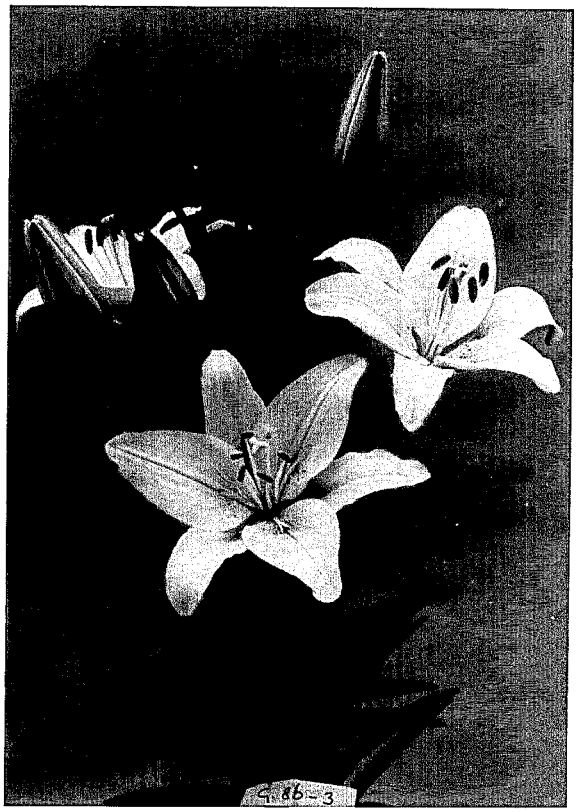
C. 86-3